US007659521B2

(12) United States Patent
Pedroni (10) Patent No.: US 7,659,521 B2
(45) Date of Patent: Feb. 9, 2010

(54) SYSTEM FOR TAKING WIDE-FIELD BEAM-EYE-VIEW (BEV) X-RAY-IMAGES SIMULTANEOUSLY TO THE PROTON THERAPY DELIVERY

(75) Inventor: Eros Pedroni, Brugg (CH)

(73) Assignee: Paul Scherrer Institute, Villigen PSI (CH)

( * ) Notice: Subject to any disclaimer, the term of this patent is extended or adjusted under 35 U.S.C. 154(b) by 321 days.

(21) Appl. No.: 11/885,707

(22) PCT Filed: Apr. 14, 2005

(86) PCT No.: PCT/EP2005/003907

§ 371 (c)(1),
(2), (4) Date: Sep. 4, 2007

(87) PCT Pub. No.: WO2006/094533

PCT Pub. Date: Sep. 14, 2006

(65) Prior Publication Data

US 2008/0191142 A1    Aug. 14, 2008

(30) Foreign Application Priority Data

Mar. 9, 2005    (EP) .................................. 05005123

(51) Int. Cl.
*A61N 5/10* (2006.01)
*A61N 5/00* (2006.01)

(52) U.S. Cl. .............................. 250/396 R; 250/370.09; 250/398; 378/9; 378/65; 378/145; 600/411

(58) Field of Classification Search ................. 250/306, 250/309, 396 R, 398, 370.09, 491.1, 492.1, 250/492.3; 378/9, 65, 145; 600/411
See application file for complete search history.

(56) References Cited

U.S. PATENT DOCUMENTS

| 3,582,650 | A | * | 6/1971 | Avery ........................ 378/65 |
| 4,191,887 | A | * | 3/1980 | Brown ................. 250/396 ML |
| 5,117,829 | A | * | 6/1992 | Miller et al. ................ 600/427 |
| 5,538,494 | A | * | 7/1996 | Matsuda ........................ 600/1 |
| 5,825,845 | A | * | 10/1998 | Blair et al. ..................... 378/62 |
| 6,814,694 | B1 | * | 11/2004 | Pedroni ........................ 600/1 |

(Continued)

FOREIGN PATENT DOCUMENTS

| EP | 0 864 337 A  | 9/1998 |
| EP | 1 584 353 A1 | 10/2005 |

OTHER PUBLICATIONS

Pedroni et al.: The 200-MEV Proton Therapy Project at the Paul Scherrer Institute: Conceptual Design and Practical Realization; Medical Physics, American Institute of Physics, New York, US vol. 22, No. 1, Jan. 1995; pp. 37-53; XP000505145; ISSN: 0094-2405.

*Primary Examiner*—Bernard E Souw
(74) *Attorney, Agent, or Firm*—Laurence A. Greenberg; Werner H. Stemer; Ralph E. Locher (57) ABSTRACT

A system for an intensity-modulated proton therapy of a predetermined target volume within an object includes a proton source to generate a proton beam, a number of proton beam forming units and a beam nozzle having an outlet for the proton beam to penetrate the predetermined target volume of the object, thereby defining a cross sectional scanning exit area. The system includes further a beam bending magnet disposed upstream of the nozzle, and an x-ray tube and an x-ray imager. The x-ray tube is associated with an irradiation channel within the beam bending magnet, wherein the irradiation channel is oriented along the prolongation of the nominal proton beam direction thereby delivering the x-ray beam along the proton beam direction.

18 Claims, 4 Drawing Sheets

U.S. PATENT DOCUMENTS

| | | |
|---|---|---|
| 7,212,608 B2 * | 5/2007 | Nagamine et al. ............. 378/65 |
| 7,212,609 B2 * | 5/2007 | Nagamine et al. ............. 378/65 |
| 7,317,192 B2 * | 1/2008 | Ma ..................... 250/396 ML |
| 2002/0188194 A1 | 12/2002 | Cosman |
| 2005/0016168 A1 | 1/2005 | Singh |
| 2007/0215819 A1 * | 9/2007 | Hiramoto et al. ......... 250/492.3 |
| 2008/0191142 A1 * | 8/2008 | Pedroni ............... 250/396 ML |
| 2008/0240350 A1 * | 10/2008 | Moyers ....................... 378/65 |

* cited by examiner

FIG 3A Compact gantry G

FIG 3B long throw gantry G'

FIG 4

SYSTEM FOR TAKING WIDE-FIELD BEAM-EYE-VIEW (BEV) X-RAY-IMAGES SIMULTANEOUSLY TO THE PROTON THERAPY DELIVERY

CROSS-REFERENCE TO RELATED APPLICATIONS

The present application is a national phase application of PCT/EP2005/003907, filed on Mar. 14, 2005, which claims priority to European Application No. EP 05005123.5, filed on Mar. 9, 2005, both of which are hereby incorporated by reference.

BACKGROUND OF THE INVENTION

The invention relates to a system and a method for an intensity-modulated proton therapy of a predetermined volume within an object.

Proton therapy is an advanced method of applying cancer radiotherapy by using proton beams. It is a superior but costlier alternative to conventional therapy, which is usually applied with photon beams. Gantries for this kind of proton therapy have been published and proposed in the international patent applications WO 2001/00276 and WO 2004/026401 and in the European patent application 04 017 266.0 respectively.

In characterizing the distinction between photon beam therapy and proton beam therapy it has to be emphasized that a photon beam penetrates through the whole patient body. The dose profile is characterized by a dose maximum at about 1 cm under the skin followed by a monotonic exponential fall-off of the dose as a function of the depth. Unlike to a photon beam, a proton beam is characterized by a well-defined range of penetration of the beam with a dose maximum at the end of the range, the so-called Bragg peak. By changing the energy of the proton beam the position of the Bragg peak in the interior of the patient body can be easily controlled.

Therefore, there exist several convincing reasons for using proton therapy instead of photon therapy. Due to the well-defined localization of Bragg peaks in depth, proton therapy can provide in almost any situation a better localization of the dose to the target volume as compared to conventional therapy with photons. With this method a better sparing of the healthy tissues surrounding the tumor can be achieved. This important issue is used in difficult clinical situations, mainly when the cancer is surrounded by sensitive anatomical structures. The higher magnetic rigidity of the proton beam requires the use of bulky equipment for the accelerator and for the beam lines, which makes on the other hand this superior therapy more expensive than conventional therapy.

Modern radiotherapy is preferentially delivered on the patient lying in supine position by applying the beam from different directions using a so-called gantry. Photon gantries span a diameter of only 2 to 3 m. A proton gantry is typically 10 m long, it comprises a proton beam line mounted on a heavy rigid support (with a total weight of more than 100 tons). The rotation of the proton gantry around the patient table spans a cylindrical volume with a radius of 2 to 6 m.

Another issue of practical interest in proton therapy is the possibility to deliver the beam by using an active dynamic beam delivery, beam scanning. The scan is performed with a small proton pencil beam (with a width of <1 cm), by applying magnetic deflections to the beam in the lateral direction and by changing dynamically the beam energy to vary the proton range. The dose is literally painted to any shape in three dimensions by touching with the Bragg peak spot (delivering variable local dose through time exposure or beam intensity changes) sequentially each point on a grid within the target (conformation of the dose to the target volume).

The scanning method must be compared with the more conventional method, which is to scatter the proton beam ahead of the patient table in order to obtain an homogeneous proton fluence in the solid angle covering the tumor site. The shaping of the dose is then done in the lateral direction by using collimators and in depth by using passive ridge filters or other active modifiers like a rotating range shifter wheel (creation of a spread out Bragg peak SOBP through a spatial or time varying amount of material placed in the beam).

With proton beam scanning one can achieve a better conformation of the dose to the target volume. One can avoid the unnecessary 100% dose applied to the healthy tissue in reason of the fixed modulation of the range of the passive scattering method (constant SOBP compared to the variable SOBP of scanning, which can be varied as a function of the lateral position of the beam). The shaping of the dose is controlled completely just by computer control. There is no need to fabricate and position in the beam individually shaped hardware (the field and patient specific devices like collimators and compensators). With scanning the beam can be applied on the patient from several beam directions in sequence, without the need for the personnel to enter the treatment room (higher patient throughput to reduce costs can be achieved).

With scanning the dose distribution can be shaped to any shape, including (intentional) non-homogeneous dose distributions (with scattering a homogeneous dose is delivered by default). This possibility is the prerequisite for the delivery of the so-called intensity modulated proton therapy (IMPT), which relies on the idea to optimize the intensities of each proton pencil beam of a whole treatment all together independently of the gantry angle (simultaneous optimization of the beam spots). The constituent dose fields applied from each beam direction don't need to be homogeneous, only the sum must.

At the time of writing, the proton gantry of the Paul Scherrer Institute at 5232 villigen PSI in Switzerland (Proton therapy facility; its first beam line is there commonly known as "Gantry 1") is still the only proton facility in the world capable of delivering therapy with an active scanning of the proton beam and capable of providing patient treatments with IMPT plans. In the context of the expansion of the PSI facility, an improved gantry for beam scanning ("Gantry 2") is under construction. The invention described hereinafter is therefore an addendum to previous patents related to the design of the proton gantry of PSI dedicated to beam scanning (Patent applications as mentioned above).

However, also with the new gantry various problems in dose shaping and exact dose delivery have to be solved. One of these problems is the challenge of organ motions due to various reasons. Organ motion during treatment is therefore a severe problem faced by any kind of precision radiotherapy (including dynamic therapy with photons). In case that during the delivery of the scanned beam the target volume moves, the shape and the homogeneity of the dose distribution can be significantly disturbed, up to the point that the dynamic beam delivery can not be used at all. This is actually a main criterion for the choice of the cases treated on the Gantry 1 of PSI. Due to the organ motion problem presently at PSI only non-moving tumors attached to bony structures are treated with the beam scanning method.

A significant improvement can be achieved by increasing the speed of scanning such that the target can be repeatedly scanned (target repainting, rescanning). This has been a major point of development for the new Gantry 2 and is established accordingly. The methods envisaged to cope with the organ motion problem in the presence of large-movements like in the chest, are to switch off the beam, when the target is moved away from the desired position (gated beam delivery) or to follow directly with the pencil beam the displacement of the target (tracking). The best-known example of gating is the synchronization of the beam delivery within a given phase interval of the respiration cycle measured by external means (chest wall movement, control of the amount of inspired air etc.). The disadvantage of these methods is that the information on the target motion remains an indirect indication.

SUMMARY OF THE INVENTION

It is therefore an object of the present invention to provide a system and a method for the delivery of an intensity modulated proton therapy which copes with the problems caused by undesired movements of the target volume thereby allowing a more direct indication to these movements.

These objectives are achieved according to the present invention by a system for an intensity-modulated proton therapy of a predetermined target volume within an object, comprising:
a) a proton source in order to generate a proton beam;
b) a number of proton beam bending and/or focusing units;
c) a beam nozzle having an outlet for the proton beam to penetrate the predetermined target volume of the object, thereby defining a cross sectional scanning exit area;
d) a beam bending magnet being disposed upstream of the nozzle;
e) an x-ray tube and an x-ray imager wherein the x-ray tube is associated with an irradiation channel within the beam bending magnet; said irradiation channel being oriented along the prolongation of the nominal proton beam direction thereby delivering the x-ray beam along the proton beam direction.

The corresponding method according to the present invention is a method for delivering an intensity-modulated proton therapy to a predetermined target volume within an object, comprising the steps of:
a) providing a proton source in order to generate a proton beam;
b) providing a number of proton beam bending and/or focusing units in order to bend and/or focus the proton beam in a predetermined manner;
c) providing a beam nozzle having an outlet for the proton beam in order to penetrate the predetermined target volume of the object with the proton beam,
d) providing a beam bending magnet being disposed upstream of the nozzle;
e) applying an x-ray beam along an irradiation channel within the beam bending magnet; said irradiation channel being oriented along the prolongation of the nominal proton beam direction in order to deliver the x-ray beam along the proton beam direction to the target volume.

The solutions according to the present invention, which provide the high precision and reliability for observing directly target motion and facilitating the option for applying tracking or gating onto a tumor with may optionally marked with clips, is the use of pulsed X-rays (i.e. shooting at a few Hz). It is therefore possible to work along all three objectives (rescanning, gating and tracking). The subject of the present invention is focused on the subject of taking X-ray images for providing direct information on organ/target movements for the purpose of precise gating or tracking.

A preferred embodiment of the present invention comprises a couple of sweeper magnets being disposed upstream of said beam bending magnet in order to sweep the proton beam in both lateral directions before the proton beam enters into the beam bending magnet, and said sweeper magnets and/or said beam bending magnet are controlled in order to guarantee a parallel beam orientation over the complete cross-sectional scanning area. Therefore, any optical parallaxes can be avoided since the proton beam stays parallel to the nominal axis over the complete cross-sectional scanning area which allows also the objective of field patching. Further, the same angular opening in the beam bending magnet can be used for protons and X-rays.

Simultaneous adaptation of the proton beam can be achieved by delivering the x-ray beam simultaneously to the proton beam.

A preferred position for the x-ray imager may be its disposal downstream of the target volume within said object as seen downstream in the direction of the proton beam. The x-ray imager may constitute e.g. part of a patient table on which a patient lays in supine position for proton beam therapy. In a further preferred embodiment the x-ray imager is mounted on a moving extension of the nozzle, since this extension remains oriented on the beam axis independently of and during gantry rotations.

For determining motions of the target volume or for tracking its motion, a preferred embodiment may comprise first means for determining the position of the target volume relative to the beam orientation is provided; said first means comprising second means for determining the position of an anatomical landmark and/or an additional marker applied to the object whereby the position of the anatomical landmarks and/or the additional marker relative to the target volume is known by evaluating the image gained from the x-ray imager. Alternately, the relation between the target volume and other anatomical landmarks and/or clips can be established already during the phase of treatment planning using 3d images in a computer tomography. It can be stressed that nowadays the most modern computer tomography offer time resolved images (4d-CT). It is therefore of both great importance and benefit to be able to observe the motion of the anatomical landmarks and/or clips during the treatment. The relations between clips/landmarks and target volume can then also be reassessed with X-rays when the patient is in treatment position. This is also of great benefit considering that this problem of organ motion has to be repeatedly observed at each fraction of a fractionated treatment which comprises easily 20 to 30 treatment sessions.

Accordingly, the sweeper magnets and/or said beam bending magnet may be controlled in order to compensate a movement of the target volume to be treated by applying compensation data to the control means of the sweeper magnets and/or the beam bending magnets, said compensation data gained from the determination of the position of the target volume. Of course, this feature further allows to design said first means for determining the position of the target volume as means for tracking any lateral movement of the target volume.

In order to provide a more conformal dose distribution and to spare dose on the healthy tissue from the continuous application of X-rays in an optimal manner the proton beam may be delivered in synchronization either aligned with an expected movement of the target object, such as the chest movements due to the breathing cycle, or aligned the an expected non-movement of the target object, such as during the idle periods of the breathing cycle. This allows for instance to limit the x-ray shooting to only one image that is taken randomly at different times within the gating period applied to the beam, trigged for example by a chest movement sensing or breathing air flow sensing. Accordingly, also the proton beam is delivered discontinuously according to the desired synchronization.

Further advantages of the present invention may be present in the additional depending claims.

BRIEF DESCRIPTION OF THE SEVERAL VIEWS OF THE DRAWINGS

Preferred embodiments of the present invention are described below with reference to the following drawings. They depict.

DETAILED DESCRIPTION OF THE INVENTION

Figure 1:
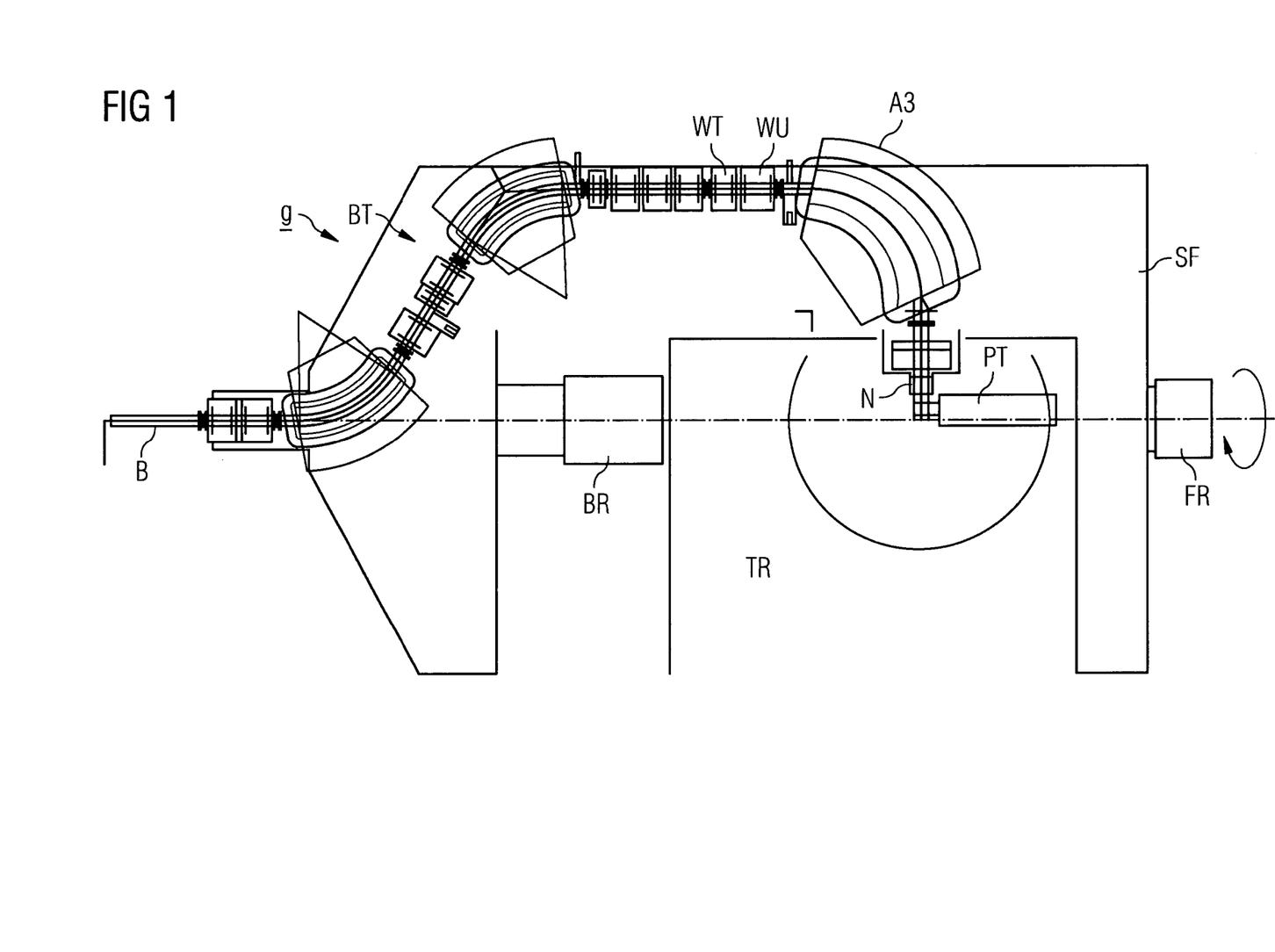
FIG. 1 a schematic cross sectional view on a gantry system.

FIG. 1 is a schematic top view on the cross section of a gantry G for the illustration of its mechanical layout. A proton beam B is generated in a non-illustrated accelerator, such as a cyclotron (but synchrotron, linear accelerator or others are possible as well), which is adjustable with respect to the intensity of the beam B. For directing the beam B to an object, such as a patient or a biological probe volume, a beam transport system BT is installed within a support frame SF. The support frame SF is pivoted with a front roll FR and a back roll BR. The beam transport system BT is supposed to rotate only on one side of the gantry G by ±95°. Therefore, a patient table PT is mounted independently from the gantry G and is accessible from one side of the treatment room TR which enables the medical personal to access to the patient at any time through a permanent fixed floor.

Further, medical equipment favorable to the medical therapy, like CT, anesthesia devices etc. can be disposed at any time very close the patient table PT. A nozzle N located utterly downstream of the beam transport system BT can be located-very close to the patient, too, achieving remarkably benefits to the sharpness of the proton beam B in the target volume. From the patient table PT, the patient experiences the treatment room TR more or less as a room having normal dimensions with a small rotating nozzle N with a sliding cover extending inside this treatment room TR. The patient sees only the nozzle N rotating along a slit in the half cylindrical internal wall of the treatment room TR. With this design the need of a moving floor (except for the slit of the nozzle N) is canceled. The treatment room TR has for example a length of 6 to 7 m, depth of 5 to 6 m and a height of 2.2 to 2.4 m. These dimensions of the treatment room TR even facilitates the horizontal rotation of the patient table PT along its horizontal axis.

Figure 2:
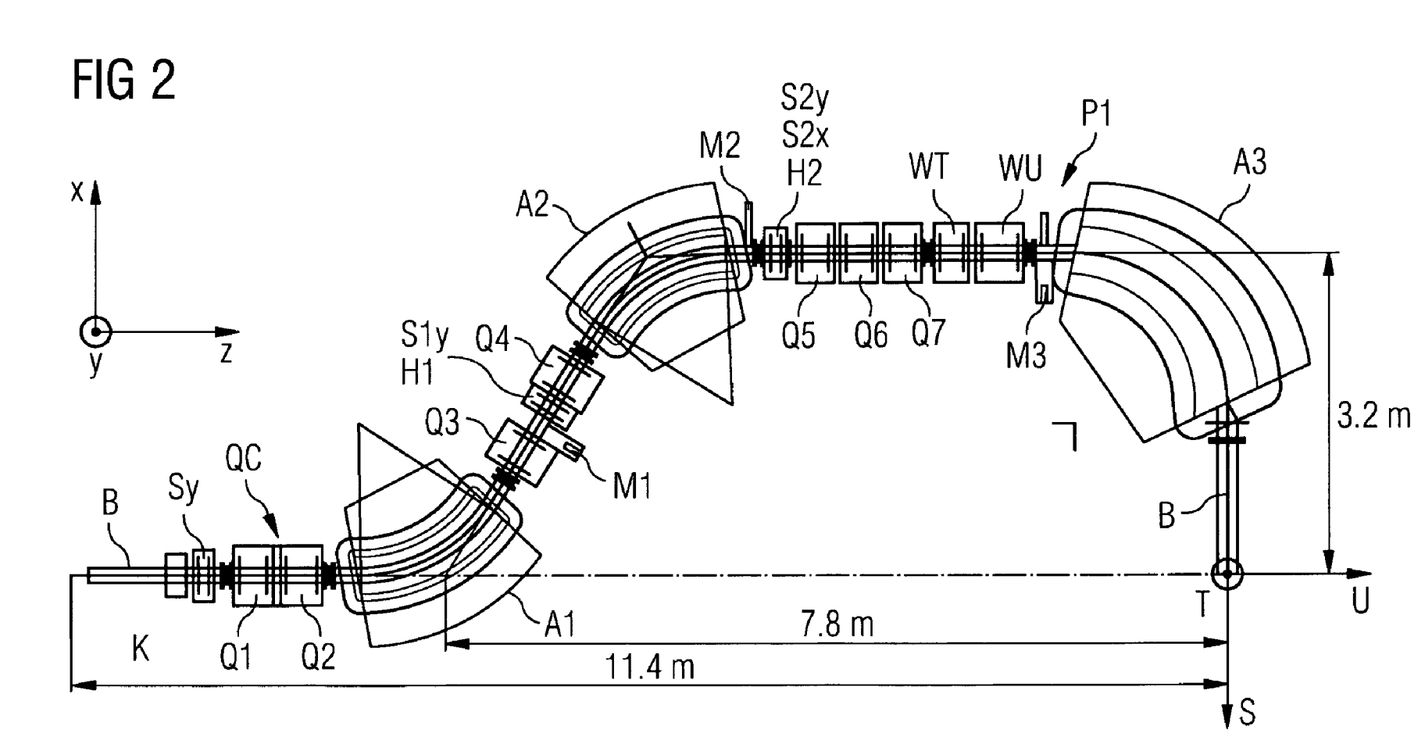
FIG. 2 a schematic cross sectional view on the beam optical components of the gantry system illustrated in FIG. 1.

The beam transport system BT used for the application of the proton beam B to the target volume within a patient is schematically shown in FIG. 2. This beam transport system BT comprises a system of three dipoles A1, A2, A3 and seven quadrupols Q1 to Q7. Other elements are steering magnets Sx/y (some of those elements are embedded as separate windings in the sextupoles H), optional slits or fixed collimators K, beam diagnostic elements M and vacuum pumps P. The main dynamic elements for the scanning are the two sweeper magnets WU and WT and a dynamic quadrupole corrector QC.

The beam optics calculations were performed for a nominal beam energy of 230 MeV (other energies are obtained by scaling the electric current in the magnetic elements of the beam line according to the momentum of the beam). The bending radius applied to the beam B is chosen to 1.5 m. The nominal field is B=1.5 Tesla. The radial parallel displacement of the beam line from the rotation axis is about 3.2 m. The distance of the exit field boundary of the 90° bending magnet to the isocenter is approx. 1.7 m. This space available in this embodiment is sufficient for keeping the bulk of the 90° bending magnet A3 during rotation to stay outside of the treatment room TR at a distance of about 1.2 m from the isocenter, in order to keep the ceiling of the treatment room TR at least 2.4 m high (normal room height) which is a significant improvement for the mental well-being of the patient. The shape of the beam line is derived from these settings, by using the minimal space necessary to place all beam transport elements needed to fulfill the beam optics requirements inside the most minimal space of the support frame SF. This beam transport system BT offers therefore the full parallelism of the beam B during painting, a true size imaging from the starting point of the rotating beam line (gantry coupling point) to the isocenter (the end point where the beam is scanned in the patient). Further, beam achromatism and beam focus invariance during double sweeping in U- and T-direction is achieved.

The beam delivery elements disposed upstream of the beam transport system BT are not shown. A cyclotron delivers a continuous beam being adjustable with respect to its intensity. The change of the energy will be preferentially done by changing dynamically the setting of a degrader and the tune in the beam line ahead and on the gantry G. Between the cyclotron and the degrader a fast kicker magnet is mounted for the switching ON and OFF of the proton beam B with a reaction time of only 50 μs.

Figures 3, 3A:
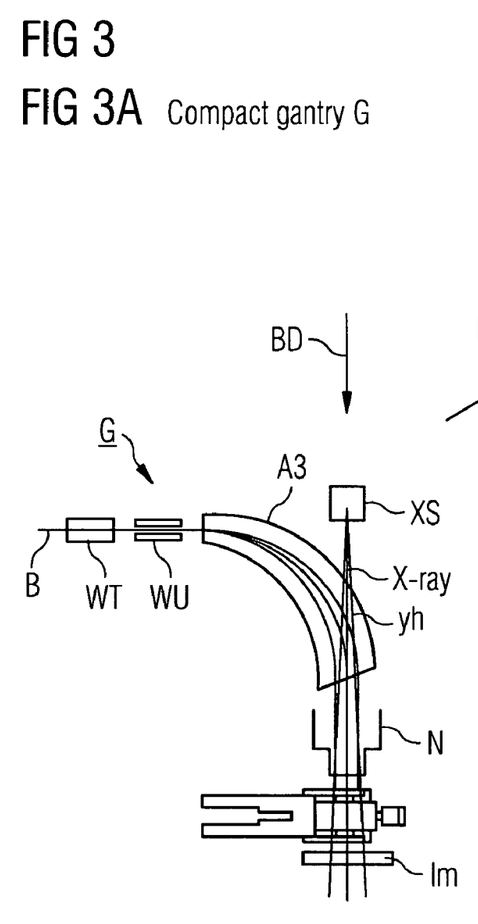
FIG. 3 a schematic cross sectional view on two gantry systems having a yoke hole for x-ray radiation in the last beam bending magnet.

According to the present invention, a system is described according to FIG. 3 which permits to take X-rays pictures originating from an X-ray source XS along the beam direction BD simultaneously with the proton beam delivery. The position resolution of an X-rays imager Im is usually quite good, the acquired information is probably the best that one can have. The algorithm for tracking the movement of clips attached to the tumor (or tracking other anatomical structures if visible) is quite simple and can be therefore used to control the beam bending and/or focusing units. The major advantage of using BEV images is then to be able to relate the motion of the clips directly to a correction for the proton beam B. The precision of the correction applied to the beam B is therefore very good.

If the dose burden of taking X-ray images all the time over the full period of a treatment would come out to be unacceptable, the proposed system can come along in combination with respiration gating via external signal (air flow etc.). The X-rays would then be taken at the beginning of the treatment to synchronize and adjust the external signal to the proper position of the target and the data taking could be repeated from time to time during beam delivery (X-rays triggered at the beginning and the end of the gate) to check that the correspondence between external respiration gating and actual target position is maintained (use as quality control). The dose burden of the X-rays depends clearly on the total time of the treatment. Of course, a fast scanning system helps much in this context.

In a preferred embodiment of the present invention, the main components of the invention are:
1) Use of a dynamic proton beam delivery by pencil beam scanning on a rotating gantry G, G'.

The new gantry system of the Gantry 2 of PSI is based on the experience of using the first prototype, Gantry 1. On Gantry 2, a 2d magnetic (parallel) scanning of the proton pencil beam will be used for the spreading of the beam in the two lateral directions T and U (sweeper magnets WT, WU). For the modulation of the range the energy of the beam B (in the beam line ahead of the gantry G, G')) is dynamically changed.

2) The lateral scanning is activated by two steering magnets WT, WU placed before the last 90° bending magnet A3 (to achieve a compact gantry with a reduced diameter)

The beam scanning is started before bending the beam towards the target volume, i.e. a tumor within a patient (the T and U sweepers WT, WU are placed before the 90° bending magnet A3). The scanning of the proton beam B is parallel in both directions and the area of scanning is rather large, i.e. 12 cm×20 cm on the PSI Gantry 2 prototype.

3) The X-ray tube XS is mounted on the backward prolongation of the 90° bend exit beam axis (irradiation through a hole Yh in the yoke of the 90° bending magnet A3—hereinafter referred to as a yoke-source).

The 90° bending magnet A3 with a hole Yh (irradiation channel for the x-ray beam) in the yoke (FIG. 3a) is build along the prolongation of the exit axis of the beam B and the X-ray imager Im is mounted below the patient using a support similar to the one shown in FIG. 4. The holder is very similar to the support used for the equipment for proton radiography in the beam of our first Gantry 1. That a hole can be made in the yoke without spoiling the quality of the magnetic field has been evaluated recently.

The protons are charged particles, they are bent in the 90° bending magnet A3 by the magnetic field of this magnet. The X-rays (photons) are created outside of the magnet (no field) and since they are neutral particles they are not disturbed when they traverse the magnetic field region. It is thus possible to apply both beams B, X-ray onto the patient simultaneously along the same beam axis BD.

By having a rather large distance of the yoke-source to the patient, the divergence of the X-rays is only moderate. The geometries of both beams are thus very similar, i.e. quite close to the parallel projection aimed for the proton beam. In fact, for the scope of this invention, it could be alternately considered to even think to abandon the parallelism of the proton beam and to adjust the divergence of the exiting proton pencil beams to match exactly with the geometry of the X-rays. Anyway, it is preferred to have on Gantry 2 a perfect parallelism of the proton beam for other reasons, which are not discussed here (field patching etc).

A proton beam B used for therapy is always stopped in the patient. Therefore, the protons will never reach the imager Im and affect the quality of the X-ray image. A problem may slightly come from scattered neutrons produced by protons in the patient and emitted preferentially in the forward direction, since these in the long range could produce radiation damage to the X-ray equipment. Anyway, an influence of the neutrons on the quality of the X-ray picture as such has not been observed yet.

With such an arrangement it is now possible to apply both therapeutic protons and diagnostic photons—along the same beam axis—and at the same time.

Advantages of using a yoke-source (BEV X-ray equipment permanently installed):

The yoke-source gives the possibility to watch the position and movements of the patient during beam delivery (to observe motion of organs, and to apply beam delivery with synchronization with phase of breathing or active tracking of the beam). The most important (preferred) direction to see target movements is in the beam direction BD. Movements in the longitudinal direction have little influence on the dose distribution (no influence at all in the case of a parallel proton beam, if one neglect density heterogeneities and organ distortions). Any lateral movement of the target can be detected on a single image and the observed target displacement can be directly linked to an active correction for the scanned proton beam (tracking of the lateral tumor motion with the beam without the presence of parallax errors). Another possible advantage of the proposed solution could be seen in the fact, that radio-opaque markers needed in the images, if one wants reference to absolute coordinates, could be mounted directly in the nozzle and not on the imager itself (instead of this one can identify parts of the proton equipment itself, like the geometrical boundaries of the strip monitor, or the strips themselves). In this way, the mechanical precision required for positioning the imager support behind the patient could be correspondingly strongly relaxed (less expensive mechanics).

The use of the present invention in the context of scanning yields another considerable advantage. The X-rays can be taken simultaneously to the proton delivery while maintaining the field of view completely opened (since we don't have any limitation of the field of view due to a collimator). With photon therapy and with proton therapy by passive scattering a collimator (and optionally a compensator) need to be placed in front of the patient. Thus, only those anatomical landmarks can be seen which are inside the projection of the proton dose field (the image is bounded by the collimator opening). With a scanning system like Gantry 2 of PSI, where this invention is realized, one will not use collimators in front of the patient at all (this is already the case for the treatments applied on Gantry 1). It will thus be possible to observe organ motion and measure displacements of the target via implanted clips or other landmarks placed outside of the target volume. (The implanted clips should be kept outside the tumor to avoid tumor cells spreading in the healthy tissues when implanting them. If the clips are outside of the target, a collimator, if present, could potentially mask them).

In this sense the present invention not only recovers a big disadvantage of proton therapy, which is the lack of availability of portal imaging commonly used in photon therapy, but it overcomes this deficit by allowing to observe anatomical structures also outside of the projected target contours.

Comparison with other Similar Systems a) Comparison with conventional therapy with X-rays In the case of X-rays the beam penetrates the whole patient and exits from the other side of the patient. From the point of view of the dose to the patient this is a big disadvantage, because healthy tissues receive unnecessarily a very high dose (this dose is much higher than what is needed for diagnosis purposes with low energy x-rays). With proton therapy one can deliver more dose to the target and less dose to the healthy tissues. The dose burden to the healthy tissues is thus reduced by a factor of 2-5 with protons compared to photons.

With photons one can on the other hand use portal imaging The fact that the photons exit from the patient is used in conventional therapy for placing detectors on the exit path of the beam. This method is called portal imaging, a method used in conventional therapy in almost any hospital.

Since the protons stop in the target, portal imaging is not available with proton therapy.

The detector used with this invention is designed as a portal imaging for proton therapy, realized by applying two different beams, protons B and low energy photons X-ray, simultaneously along the same beam axis BD. The dose for diagnostics (from the low energy X-rays) is much lower than using the high-energy photons for therapy.

The present invention could be thus defined as a "portal imaging substitute for proton beam therapy". The advantage of the proposed system compared to photon therapy is that the images are not restricted through the opening of a collimator.

Figure 3B:
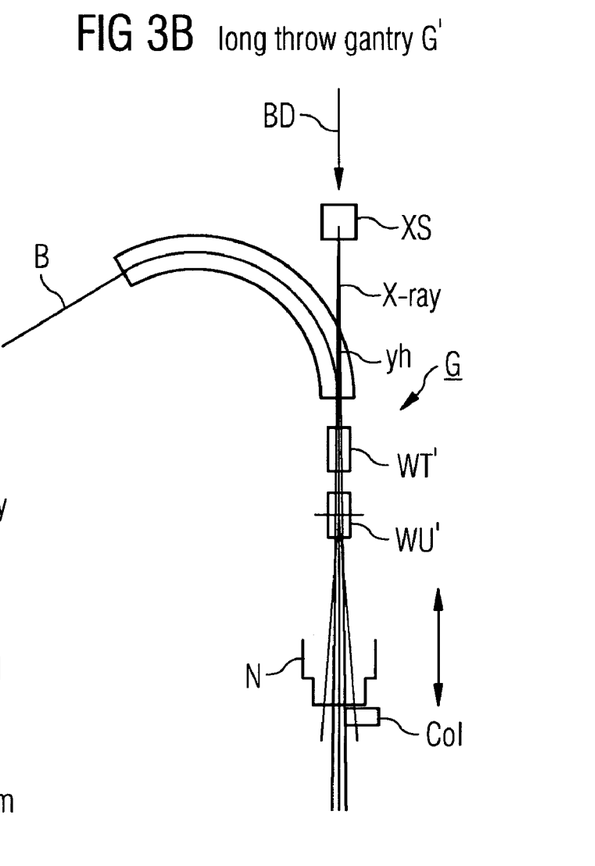

The advantage of using a yoke source in connection with upstream scanning (i.e. on a compact gantry layout) is now apparently. It can be considered that a preferred embodiment uses a gantry for scanning, where the scanning is started before the last bending magnet A3. The yoke source can therefore be used in several embodiments:

a) Use of a yoke-source on a proton gantry with beam delivery by passive beam scattering If scattering is used (the state of the art industrially available in the proton therapy field) the beam is usually scattered from a point like proton source placed after the last bending magnet (it is probably too difficult to achieve a good homogeneity of the dose by scattering the beam ahead of the last bend). The equipment used for scattering the beam is usually small in size (one wants a very sharp point-like apparent proton source after the last bend). The equipment for spreading is very likely to interfere with the X-rays, if these are applied through the hole Yh in the yoke of the last bending magnet A3. The arrangement according to the present invention is of limited use with scattering, because the equipment for scattering the beam is likely to mask the X ray field. The major advantage of the system according to the invention with scanning compared to scattering is that the images are not restricted by the opening of a collimator.

b) Use of a yoke-source on a proton gantry with beam scanning started after the last bend (FIG. 3b)

In this case the gap of the last bending magnet is usually chosen to be small. The sweeper magnets WT', WU' are mounted in the beam path of the X-rays. The gap of these magnets is usually small (5 cm) to avoid limitations on the scanning speed and to reduce power consumption. The X-rays shining through a magnet yoke hole in the last bending magnet are likely to be partly masked by the scanning equipment placed after the last bending magnet. This solution is in principle feasible but with possible restrictions.

c) Use of a yoke-source in a horizontal proton beam line

One usually has a lot additional equipment downstream of the last bending magnet, like quadrupoles, scanning magnets and other devices interfering with the field of view of the X ray tube. This situation is similar to b).

The limitations mentioned in a), b and c) are probably the reason why the proposition to take X-ray images in the BEV direction simultaneously with the proton beam has not been found so far.

d) Use of a yoke-source with scanning started after the last 90° bend (compact gantry)

In this case, there is no material (of relevance) in the beam path of the X ray field. For example, the free area is at least 17 cm×25 cm when using the data for the Gantry 2 of PSI. The material in the beam consists only of air, the vacuum window and the thin mylar foils of the beam monitors. This amount is essentially transparent to the proton beam and can be considered as not interceptive for the X-rays as well. The free area for the X-rays (the field of view) is large enough to observe anatomical structures over a reasonably large area.

If solutions a), b) and c) can be judged to be feasible with restrictions, solution d) seems to be the most optimal for this task.

Therefore, it can be summarized that the proposed arrangements b), c) and in particular d) represent the best possible arrangement for observing and correcting on-line target motion, by optionally correcting dynamically the position of the proton beam, on the basis of the data of BEV X-ray images taken during beam delivery.

In FIG. 3a) the proton beam B is coming from the left. The lateral spreading of the proton beam is by magnetic deflection in the two sweepers magnets WT,WU acting on the beam B before it is bent in the 90° bending magnet A3 in direction to the patient. With this configuration little material is disposed in the beam B. The X rays expand trough the hole Yh in the yoke of the 90° bending magnet A3 simultaneously to the proton beam B. This is the substantially most preferred layout.

In FIG. 3b) the same situation is shown for a long throw gantry. If one uses scanning one can use the same approach as in FIG. 3a), provided that the gaps of the sweepers magnets WT', WU' are large enough for the transmission of the X-ray field. In the case of scattering one has to face possible limitations due to the scattering equipment in the path of the beam and the restrictions given by the collimator opening (one should remember that moved tumors are usually small targets).

Figure 4:
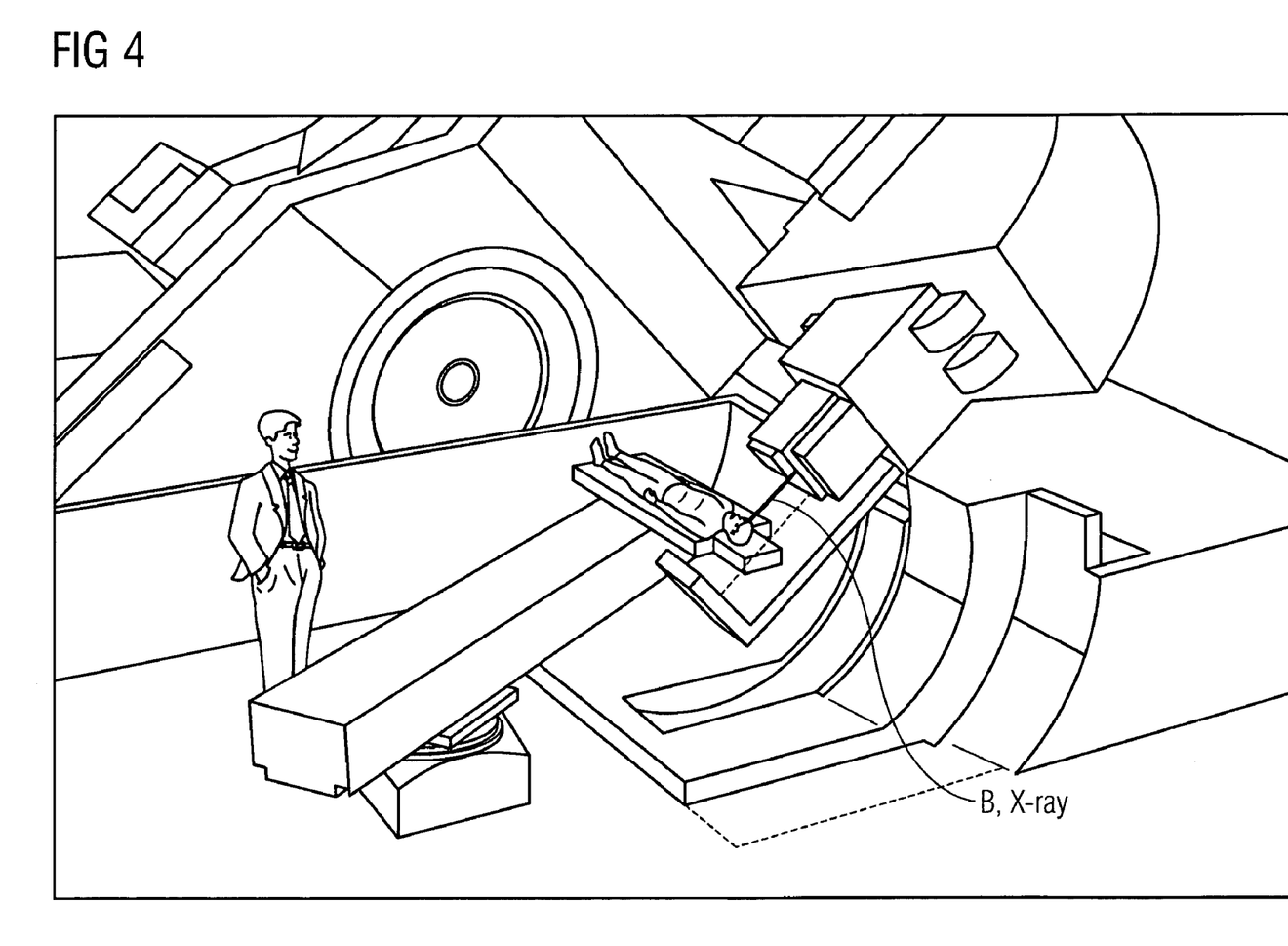
FIG. 4 an artist view of the treatment table with a removable BEV imager as it is realized in the gantry system according to the FIGS. 1 and 2.

FIG. 4 is for the sake of illustration an artist view of the treatment table with a removable BEV imager as it is realized on the Gantry 2 of PSI.

The invention claimed is:

1. A system for an intensity-modulated proton therapy of a predetermined target volume within an object, comprising:
a proton source in order to generate a proton beam;
a number of proton beam forming units;
a beam nozzle having an outlet for the proton beam to penetrate the predetermined target volume of the object, thereby defining a cross sectional scanning exit area;
a beam bending magnet being disposed upstream of the nozzle; and
an x-ray tube and an x-ray imager wherein the x-ray tube is associated with an irradiation channel within the beam bending magnet; said irradiation channel being oriented along a prolongation of a nominal proton beam direction thereby delivering an x-ray beam along a proton beam direction.

2. The system according to claim 1, further comprising:
a couple of sweeper magnets being disposed upstream of said beam bending magnet in order to sweep the proton beam in both lateral directions before the proton beam enters into the beam bending magnet, wherein
said sweeper magnets and said beam bending magnet are controlled in order to guarantee a parallel beam orientation over the complete cross-sectional scanning exit area.

3. The system according to claim 1, wherein
the x-ray beam is delivered simultaneously to the proton beam.

4. The system according to claim 1, wherein
the imager is disposed downstream of the target volume within said object as seen downstream in direction of the proton beam.

5. The system according to claim 1, further comprising
first means for determining a position of the target volume relative to a beam orientation,
said first means comprising second means for determining a position of an anatomical landmark and/or an additional marker applied to the object whereby the position of the anatomical landmarks and/or the additional marker relative to the target volume is known by evaluating an image gained from the x-ray imager in treatment position; said image being in addition optionally compared to 4d images
taken previously with a CT.

6. The system according to claim 5,
wherein said sweeper magnets and/or said beam bending magnet are controlled in order to compensate a movement of the target volume to be treated by applying compensation data to control means of the sweeper magnets and/or the beam bending magnets, said compensation data gained from the determination of the position of the target volume.

7. The system according to claim 5, wherein said first means for determining the position of the target volume are means for tracking any lateral movement of the target volume.

8. The system according to claim 1, wherein the proton beam is delivered in synchronization with one of an expected movement of the target object and an expected non-movement of the target object.

9. The system according to claim 8, wherein the proton beam is delivered discontinuously according to a desired synchronization.

10. A method for delivering an intensity-modulated proton therapy to a predetermined target volume within an object, comprising the steps of:
providing a proton source in order to generate a proton beam;
providing a number of proton beam forming units in order to form the proton beam in a predetermined manner;
providing a beam nozzle having an outlet for the proton beam in order to penetrate the predetermined target volume of the object with the proton beam,
providing a beam bending magnet being disposed upstream of the nozzle; and
applying an x-ray beam along an irradiation channel within the beam bending magnet; said irradiation channel being oriented along a prolongation of a nominal proton beam direction in order to deliver the x-ray beam along a proton beam direction to the target volume.

11. The method according to claim 10, further comprising the steps of:
providing a couple of sweeper magnets being disposed upstream of said beam bending magnet in order to sweep the proton beam in both lateral directions before the proton beam enters into the beam bending magnet, and controlling said sweeper magnets and/or said beam bending magnet in order to guarantee a parallel beam orientation over a complete cross-sectional scanning area defined by the nozzle.

12. The method according to claim 10, further comprising delivering the x-ray beam simultaneously to the proton beam.

13. The method according to claim 10, further comprising disposing the imager downstream of the target volume within said object as seen downstream in direction of the proton beam.

14. The method according to claim 10, further comprising determining a position of the target volume relative to the beam orientation by determining a position of an anatomical landmark and/or an additional marker applied to the object whereby the position of the anatomical landmarks and/or the additional marker relative to the target volume is known by evaluating an image gained from the x-ray imager.

15. The method according to claim 14, further comprising controlling said sweeper magnets and/or said beam bending magnet in order to compensate a movement of the target volume to be treated by applying compensation data to control means of the sweeper magnets and/or the beam bending magnets, thereby gaining said compensation data from the determination of the position of the target volume.

16. The method according to claim 14, further comprising using the determination of the position of the target volume for tracking any lateral movement of the target volume.

17. The method according to claim 10, further comprising delivering the proton beam in synchronization with one of an expected movement of the target object, and an expected non-movement of the target object;.

18. The system according to claim 17, further comprising delivering the proton beam discontinuously according to the desired synchronization.

* * * * *